US00PP22097P3

(12) United States Plant Patent

Werner et al.

(10) Patent No.: US PP22,097 P3

(45) Date of Patent: Aug. 30, 2011

(54) *CERCIS* PLANT NAMED 'RUBY FALLS'

(50) Latin Name: *Cercis canadensis*
Varietal Denomination: Ruby Falls

(76) Inventors: Dennis James Werner, Raleigh, NC (US); Layne Karlton Snelling, Cary, NC (US)

( * ) Notice: Subject to any disclaimer, the term of this patent is extended or adjusted under 35 U.S.C. 154(b) by 0 days.

(21) Appl. No.: 12/653,832

(22) Filed: Dec. 21, 2009

(65) Prior Publication Data

US 2010/0205703 P1 Aug. 12, 2010

Related U.S. Application Data

(60) Provisional application No. 61/207,216, filed on Feb. 10, 2009.

(51) Int. Cl.
*A01H 5/00* (2006.01)

(52) U.S. Cl. ..... Plt./216

(58) Field of Classification Search ..... Plt./216
See application file for complete search history.

(56) References Cited

U.S. PATENT DOCUMENTS

PP8,640 P * 3/1994 Hosage, Jr. ..... Plt./216
PP18,528 P2 * 2/2008 Bennett ..... Plt./216

* cited by examiner

*Primary Examiner* — June Hwu

(57) ABSTRACT

*Cercis* 'Ruby Falls' is a new and distinct variety of redbud that has the following unique combination of desirable features that are outstanding in a new variety.

1. Weeping growth habit.
2. Ease of asexual propagation using chip-budding.
3. Emerging foliage with deep purple color, transitioning to burgundy and eventually green during the growing season.
4. Bright purple flowers produced in abundance during the spring.

3 Drawing Sheets

Latin name of the genus and species: Genus: *Cercis* (Leguminosae). Species: *Cercis canadensis* (eastern redbud).

Cultivar denomination: The inventive cultivar of *Cercis canadensis* disclosed herein has been given the cultivar denomination 'Ruby Falls'.

BACKGROUND OF THE INVENTION

The present invention relates to a new and distinct cultivar of *Cercis* (redbud) grown as an ornamental tree for home and commercial landscapes. Redbud is typically grown as a small tree for its attractive purple flowers that are borne in the spring, and sometimes for its interesting foliage color (purple, variegated, or golden leaf forms) or architectural form.

The new and distinct cultivar of redbud resulted from a formal breeding program established by the inventors in Raleigh, N.C., United States. One of the objectives of the breeding program was to develop a purple-leaf form of redbud that exhibited the weeping growth habit. 'Ruby Falls' originated as a second generation descendant from a controlled cross (using caged trees and bumblebees) of *Cercis canadensis* 'Covey'×'Forest Pansy' (*Cercis canadensis*) made in 2001 in Raleigh, N.C. Trees of both cultivars established in 15-gallon pots were placed inside a screened enclosure to prevent insect visitation. A small hive of bumblebees was placed inside each cage to facilitate pollen exchange between the 2 cultivars. Redbud is widely accepted as being a self-incompatible species, thus any fruit formed are almost always the result of cross-pollination. Fruit and seed were obtained only on the 'Covey' parent. 'Covey' (U.S. Plant Pat. 10,328) was introduced in 1997 and is described as a green leafed, weeping form of *Cercis canadensis* with light purple flowers. 'Forest Pansy' (U.S. Plant Pat. No. 2,556) is a non-weeping, purple leaf form of eastern redbud (*Cercis canadensis*) discovered in 1947 in McMinnville, Tenn. Both parents are commonly available in commerce.

The first generation seeds resulting from the 2001 hybridization were harvested in fall of 2001 and germinated in a greenhouse in Raleigh, N.C. in the winter of 2002. The resulting 19 first generation seedlings were planted in a field setting at a research station in Jackson Springs, N.C., isolated from other redbuds, in spring 2002. These plants flowered in spring 2005, and second generation seed was collected that same year off of all plants that produced seed. This seed was germinated in a greenhouse in Raleigh, N.C. in December, 2005. From these approximately 400 seedlings, 42 seedlings showing dark purple leaves and weeping growth habit were selected and grown in the greenhouse in spring and summer, 2006. These 42 seedlings were later transplanted to the field in November, 2006, and one plant, later designated NC2006-8, was selected as the best individual for its purple leaf color and weeping growth habit. This original plant demonstrated characteristics identical to those subsequently expressed on other plants when propagated by chip budding. This single plant is the subject of the present invention 'Ruby Falls'.

The distinguishing traits of 'Ruby Falls' are its distinctive purple leaves in the spring, turning to burgundy and ultimately green later in the summer, and its weeping growth habit. The cultural requirements for 'Ruby Falls' are well-drained soil, full sun, and moderate moisture. 'Ruby Falls' exhibits no serious pest or disease problems known to the inventors.

The closest comparisons known to the inventors are its grandparents, 'Forest Pansy' and 'Covey', and 'Traveller' and 'Cascading Hearts', two existing cultivars in the trade. Plants and leaves of this new cultivar differ from 'Forest Pansy'. In direct comparisons of the 2 cultivars in the inventor's experimental trials, plants of 'Ruby Falls' are weeping in growth, compared to the non-weeping growth of 'Forest Pansy'. 'Ruby Falls' differs from 'Covey' grandparent in having purple leaves. 'Rudy Falls' is clearly distinct from its original grandparents. 'Ruby Falls' differs from the green leaf, weeping cultivars 'Traveller' (U.S. Plant Pat. No. 8,640) and 'Cascading Hearts' (U.S. Plant Pat. 18,528) in having purple leaves.

The first asexual propagation of 'Ruby Falls' was conducted by Alex and Harald Neubauer on behalf of the inventors in August, 2007 in Belvidere, Tenn. 'Ruby Falls' has subsequently been propagated in the same location in August, 2008. In all cases, the original plant selection was propagated asexually by chip budding in late summer onto *Cercis canadensis* rootstock. Such budded trees heal rapidly, and resume normal growth the following spring after budding. Five plants derived from chip budding of the cultivar were established in the inventor's test plots in January, 2009. During all asexual propagation, the characteristics of the original plant have been maintained. Plants derived from chip budding exhibit characteristics identical to those of the original plant, and no aberrant phenotypes have appeared.

Performance evaluation of the original plant and budded trees demonstrate this cultivar to be relatively consistent in its characteristics even under the different growing conditions associated with yearly climatic variation.

Plants of the new cultivar are vigorous after chip-budding in the nursery setting, growing up to 1.8 meters the year after fall budding. Plants are weeping in growth habit. Flowers are an attractive bright lavender color.

'Ruby Falls' is distinguished from other related known cultivars based on the unique combination of traits including weeping growth habit and purple leaf color during the spring and through mid-summer.

The new cultivar has been named the RUBY FALLS cultivar. No public sale of 'Ruby Falls' has yet taken place at the time of this application. First public sale is anticipated to occur in January, 2010.

SUMMARY OF THE INVENTION

'Ruby Falls' is a new and distinct cultivar of redbud tree that has the following unique combination of desirable features outstanding in a new cultivar. In combination these traits set 'Ruby Falls' apart from all other existing cultivars of redbud known to the inventors.

1. 'RUBY FALLS' has weeping growth habit.
2. 'RUBY FALLS' is asexually propagated using chip budding.
3. 'RUBY FALLS' has large, attractive purple leaves in the spring, turning to burgundy and ultimately green as the growing season progresses.
4. 'RUBY FALLS' has attractive, bright purple flower color.

BRIEF DESCRIPTION OF THE DRAWINGS

The photographs in the drawings were made using digital photography techniques, and show the colors as true as reasonably possible by digital photography. All photographs were taken from the original five-year-old tree growing at Jackson Springs, N.C.

DETAILED BOTANICAL DESCRIPTION OF THE VARIETY

Figure 1:
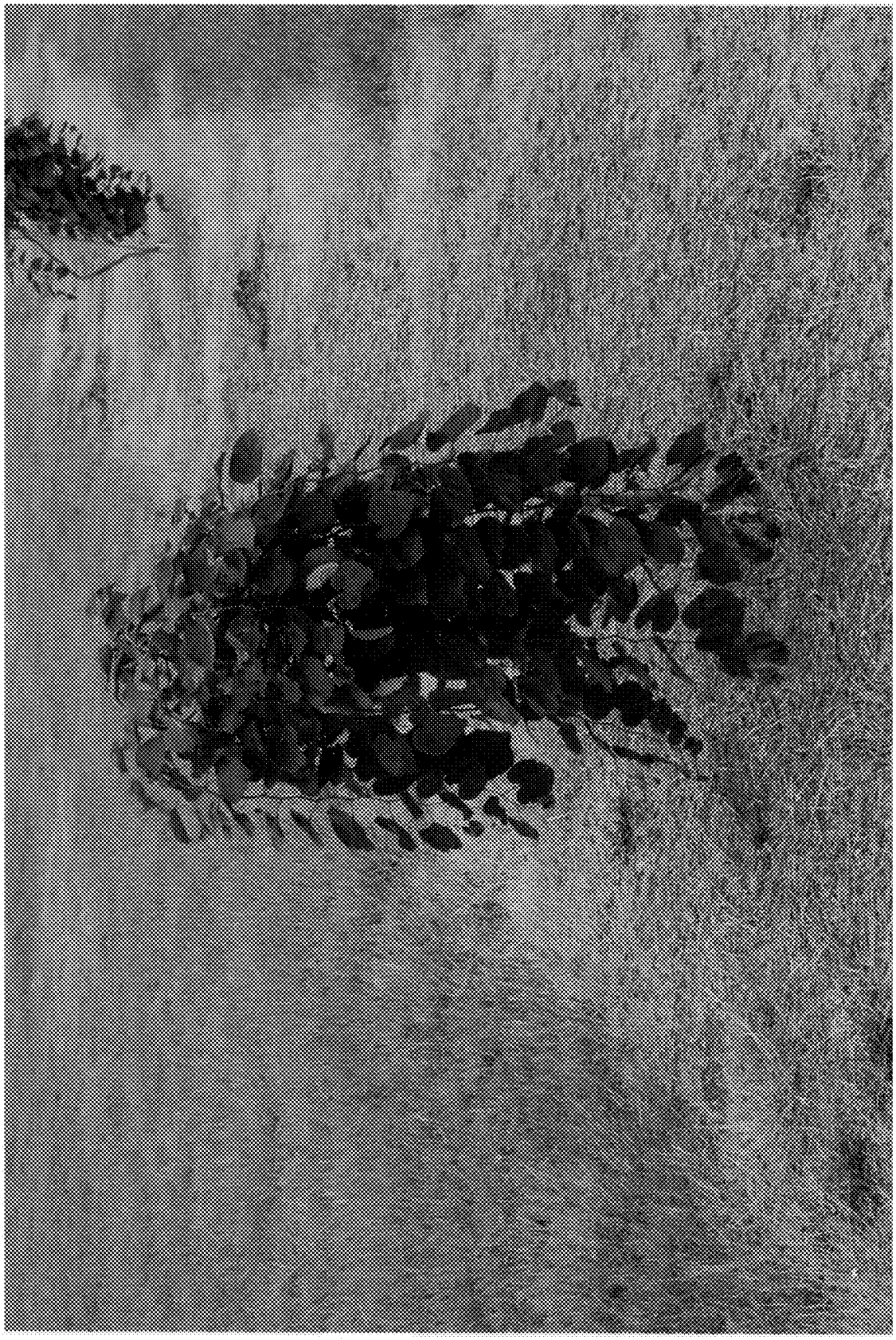
FIG. 1 shows a typical plant of 'RUBY FALLS', showing the weeping habit and purple leaves.
Figure 2:
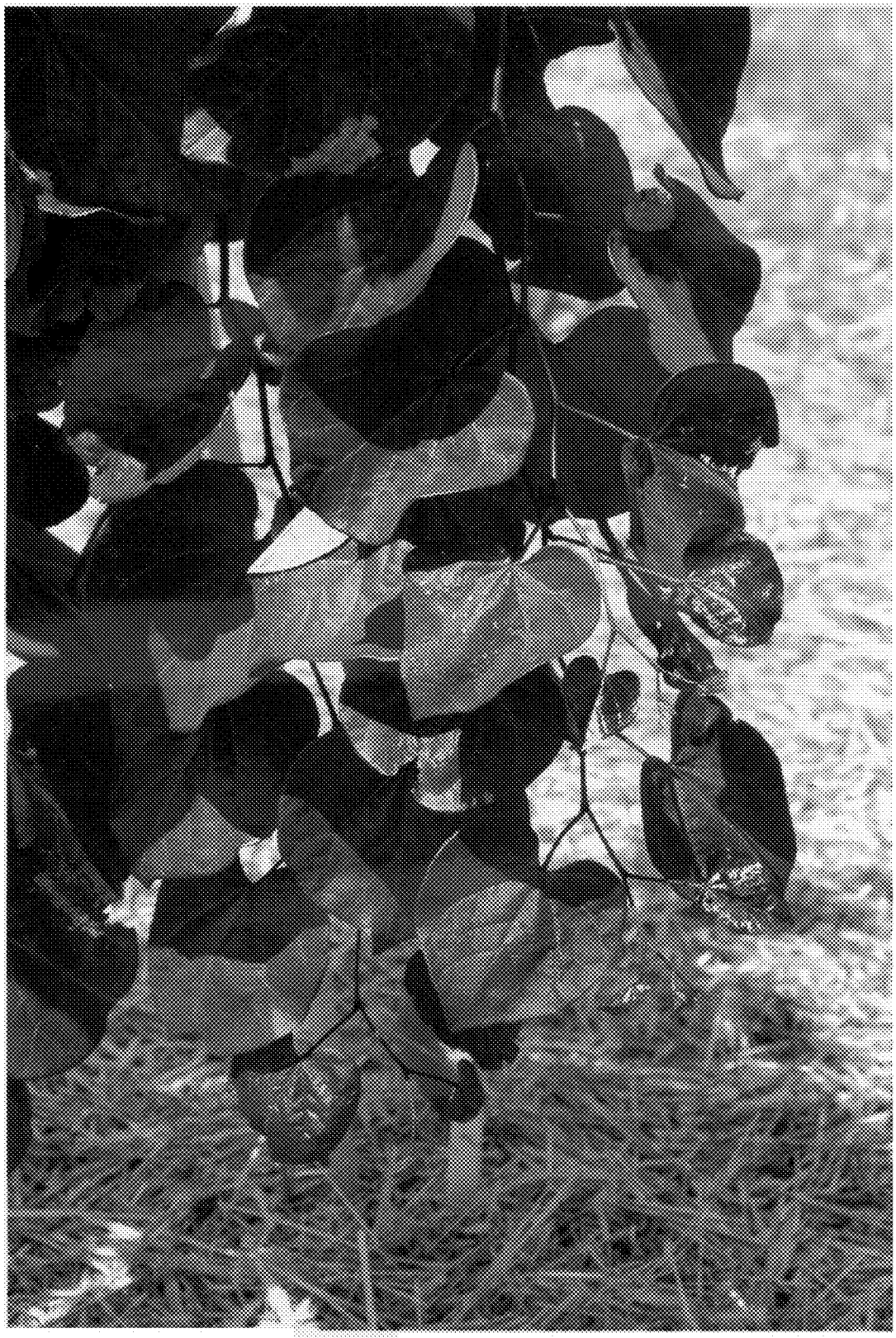
FIG. 2 shows the typical purple coloration and form of leaves of 'RUBY FALLS'. This figure shows both recently formed and older leaves.
Figure 3:
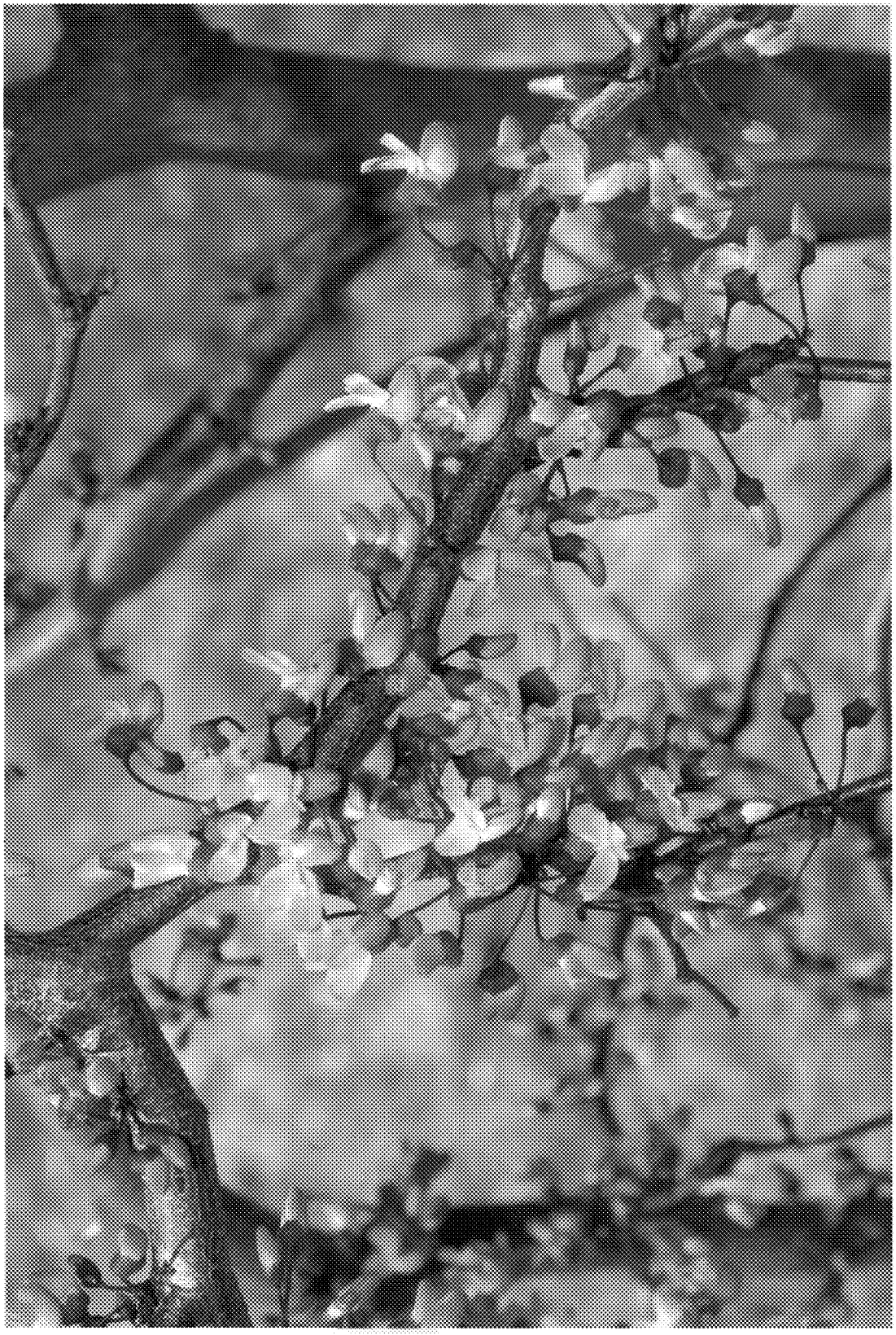
FIG. 3 shows the bright purple flowers of 'RUBY FALLS'.

The following is a detailed description of the botanical and ornamental characteristics of the subject redbud 'RUBY FALLS'. Color data are based on The Royal Horticultural Society Colour Chart, The Royal Horticultural Society, London, $5^{th}$ edition, 2007. Where dimensions, sizes, colors and other characteristics are given, it is to be understood that such characteristics are approximations of averages set forth as accurately as practicable.

The descriptions reported herein are from the original three-year-old tree growing at the research station in Jackson Springs, N.C.

Genus: *Cercis*.

Species: *Canadensis*.

Denomination: 'RUBY FALLS'.

Commercial classification: Tree, deciduous.

Common name: Redbud.

Type: Ornamental.

Uses: Small landscape tree for residential and commercial landscapes.

Cultural requirements: Full sun exposure, well-drained soil, and moderate moisture.

Parentage: Second generation selection derived from the hybridization of *Cercis canadensis* (eastern redbud) 'Covey' and *Cercis canadensis* 'Forest Pansy'.

Plant description:

*Blooming period.*—Early to mid spring, late March to early April in central North Carolina.

*Blooming habit.*—Flower buds formed both on one-year-old wood, and on older wood.

*Vigor.*—Moderate vigor.

*Plant habit.*—Weeping, well-branched.

*Height and spread.*—Height dictated by nursery management and cultural practices. Can be trained as a ground cover, or a small weeping tree typically up to six feet in height. Spread generally 2-3 feet.

*Hardiness.*—To date, hardy to negative 12.8 degrees Centigrade. Not tested below this temperature. Anticipated adapted from USDA hardiness zones 6-9.

*Propagation.*—Chip-budding onto seedling rootstock, typically in late summer in the southeastern U.S.

*Root system.*—Fibrous.

*Seasonal interest.*—Bright purple flowers in spring, and large, purple leaves from spring through mid to late summer on a weeping tree.

*Disease and pest susceptibility and resistance.*—No particular susceptibility or resistance.

*Special growing requirements.*—None. Best grown in full sun to partial shade in moderately well drained soil.

Trunk:

*Dimensions.*—0.3 m circumference measured 0.15 m above soil line.

*Bark surface.*—Slightly rugose.

*Color.*—Lighter sectors=blue-green (122D). Darker sectors=grayed-green (188A).

Stems:

*Shape.*—Stem cross section is circular.

*Length.*—Average 0.52 m of new growth yearly.

*Color.*—Yellow-green (N77A) on newly formed growth. Yellow-green (144B) on dormant one-year-old shoots. Brown (N200A) on two-year-old stems.

*Diameter.*—5 mm near terminal portion of stem on mature one-year-old stems.

*Stem surface.*—Glaucous.

*Pubescence.*—Lacking.

*Internode length.*—3.9 cm between nodes.

*Lenticels.*—Numerous, tiny. Color (N200B), measured in early spring.

*Lenticel shape.*—Circular.

Foliage:

*Type.*—Deciduous.

*Leaf arrangement.*—Alternate.

*Leaf division.*—Simple.

*Leaf shape.*—Suborbicular (immature) to broad-ovate (mature).

*Leaf base.*—Cordate.

*Leaf apex.*—Obtuse.

*Leaf venation.*—Reticulate.

*Leaf surface* (*abaxial and adaxial*).—Glaucous.

*Leaf margin.*—Entire.

*Leaf attachment.*—Petiolate.

*Petiole dimensions.*—4.1 cm length. 2.0 mm width at base tapering to 1.0 mm at apex (nearest to leaf blade).

*Petiole shape.*—Round.

*Petiole color.*—Purple (N77A) on immature leaf.

*Petiole surface.*—Smooth, lacking pubescence.

*Leaf color* (*immature leaf*).—Adaxial side=Purple (N77A). Abaxial side=Purple (59A).

*Leaf color* (*mature leaf*).—Adaxial side=N137A. Abaxial side=59A.

*Vein color* (*abaxial surface*).—Immature leaf (60A). Mature leaf (59C).

*Leaf length.*—Average length (10 leaves)=7.8 cm from leaf tip to base of midvein/apex of petiole. 8.8 cm from leaf tip to base of leaf blade.

*Leaf width.*—Average width (10 leaves)=10.1 cm.

*Foliar fragrance.*—None detectable.

*Stipules.*—None present.

*Causes for variation in color.*—Under normal sunlight, new foliage emerges deep purple (RHS N77A) that grades to burgundy (RHS N137A) to green (RHS 147A) over the growing season.

Flowers:

*Inflorescence.*—Papillonaceous flowers arranged in a small cluster.

*Number of flowers per cluster.*—3 to 7.

*Arrangement.*—Sessile clusters.

*Location.*—Nodes of previous years growth, and along older stems and occassionally the trunk (cauliflory).

*Length of bloom.*—2-3 weeks, depending on weather conditions.

*Flower length.*—1.0 cm from base of calyx to tip of keel.

*Flower width.*—3-4 mm immediately prior to anthesis.

*Flower depth.*—6 mm.

*Pedicel length.*—1.2 cm.

*Pedicel diameter.*—0.5 mm.

*Pedicel shape.*—Round.

*Pedicel color.*—Purple group (71A).

*Pedicel surface.*—Smooth.

*Flowers persistent or self-cleaning.*—Self-cleansing.

*Flower fragrance.*—Lacking.

*Lastingness of the overall inflorescence.*—2-3 weeks.

*Lastingness of an individual flower.*—3-5 days.

Flower bud:

*Shape.*—Broadly oval.

*Color.*—Purple group (N77A).

*Surface.*—Smooth.

*Diameter.*—1.0 to 1.5 mm.

*Length.*—4 to 5 mm.

Petals:

*Number.*—5, lower 2 fused to form keel.

*Petals fused or unfused.*—3 unfused, 2 fused.

*Standard* (*banner*) *color.*—Tip=Purple (N78B). Base=Purple (62D).

*Keel petal color.*—Tip=Purple (N78B). Base=Purple (62D).

*Wing petal color.*—Tip=Purple (N78B). Base=Purple (62D).

*Petal surface* (*adaxial*).—Smooth.

*Petal surface* (*abaxial*).—Smooth.

*Petal margin.*—Entire.

Calyx:

*Shape.*—Vase-shaped.

*Length.*—4 mm.

*Diameter.*—5 mm.

*Color* (*outer surface*).—Purple (71A).

*Color* (*inner surface*).—Purple (71A).

*Surface* (*inner*).—Smooth.

*Surface* (*outer*).—Smooth.

Sepals:

*Number.*—1 — fused.

*Color* (*adaxial surface*).—Purple (71A).

*Color* (*abaxial surface*).—Purple (71A).

*Surface* (*adaxial surface*).—Smooth.

*Surface* (*abaxial surface*).—Smooth.

Reproductive organs:

*Pistil.*—Dimensions: 1.0 cm length. 1-2 mm width. Color: Red-purple (59B). Surface: Smooth.

*Stigma.*—Shape: Elliptical. Length: Less than 1 mm. Width: Less than 1 mm. Color: Red-purple (59B).

*Style.*—Length: Less than 1 mm. Width: Less than 1 mm. Color: Red-purple (60D).

*Stamens.*—Number: 10. Fused or unfused at base: 9 fused at base. 1 free. Length: 8 mm. Width: Less than 1 mm. Color (filament): Red-purple (59B).

*Anthers.*—Shape: Round to slightly oblong. Length: Less than 1 mm. Width: Less than 1 mm. Color: Red-purple (59B). Immediately prior to anthesis.

*Pollen.*—Color: Yellow group (9B). Amount: Abundant.

*Ovary.*—Position: Superior. Shape: Elongate. Length: 1 cm. Width: 1.0 mm, tapering to less than 1 mm. Color: Red-purple (59B).

*Fruit.*—No fruit or seed produced to date. Lack of pod production likely due to the young age of the plant.

Herbarium voucher: A voucher of 'Ruby Falls' will be deposited into the Herbarium of North Carolina State University (NCSU) in Raleigh, N.C., USA upon patenting.

What is claimed is:

1. A new and distinct variety of redbud tree (*Cercis*) having the characteristics substantially as described and illustrated herein.

* * * * *